United States Patent [19]

Schiller et al.

[11] Patent Number: 4,630,925
[45] Date of Patent: Dec. 23, 1986

[54] COMPACT TEMPORAL SPECTRAL PHOTOMETER

[75] Inventors: Norman H. Schiller, Whitestone; Robert R. Alfano, Bronx, both of N.Y.

[73] Assignee: Hamamatsu Corp., Middlesex, N.J.

[21] Appl. No.: 437,897

[22] Filed: Nov. 1, 1982

[51] Int. Cl.$^4$ ............................................... G01J 3/30
[52] U.S. Cl. ................................... 356/318; 356/305; 356/328
[58] Field of Search .............. 356/300, 308, 309, 317, 356/318, 326, 328, 305; 250/213 VT, 458.1, 459, 461.1, 461.2

[56] References Cited

U.S. PATENT DOCUMENTS

| 4,327,285 | 4/1982 | Bradley | 250/213 VT |
| 4,461,572 | 7/1984 | Tsuchiya | 356/318 |

FOREIGN PATENT DOCUMENTS 151222 10/1981 German Democratic Rep. .................................. 356/318

OTHER PUBLICATIONS

Michel et al., Conference: *9th Annual Conference of Microbeam Analysis Society* (Summaries) Ottawa Canada, Jul. 22-26, 1974, pp. 18A-18E.
Kido et al., *J. Phys. E: Sci. Instrum.*, vol. 14, No. 3, Mar. 1981, pp. 349-354.

*Primary Examiner*—F. L. Evans
*Attorney, Agent, or Firm*—Irving M. Kriegsman

[57] ABSTRACT

A temporal spectral photometer for use in obtaining spectral and temporal information simultaneously of an ultrafast pulse of luminescent light emitted from a sample upon excitation thereof includes an excitation section and a detection section. The excitation section includes a picosecond laser for exciting the sample to emit luminescent light and imaging optics for imaging the emitted light. The detection section includes a pin hole slit through which light from the imaging optics is admitted, a streak camera tube, an optical system including a grating for forming an image of the pin hole slit on the photocathode of the streak camera tube and at the same time dispersing the light admitted through the pin hole slit into its component wavelengths, a micrometer assembly mechanically coupled to the grating for selectively changing the wavelength region of dispersed light impinging on the photocathode, a video camera, a camera lens system for imaging the output image formed on the phosphor screen of the streak camera tube onto the input end of the video camera, a digital temporal analyzer coupled to the output of the video camera for digitizing and analyzing image information from the video camera and a video monitor coupled to the output of the temporal analyzer for displaying the analyzed data.

25 Claims, 3 Drawing Figures

COMPACT TEMPORAL SPECTRAL PHOTOMETER

BACKGROUND OF THE INVENTION

The present invention relates generally to the field of spectroscopy and more particularly to an apparatus for use in obtaining high resolution spectral and temporal information simultaneously of an ultrafast pulse of luminescent light on a $10^{-14}$ to $10^{-2}$ second time scale.

The study of picosecond luminescence phenomenon requires an instrument which simultaneously measures both spectral as well as temporal information.

It is well known that one can obtain intensity versus wavelength information of a light pulse using a spectrograph. It is also well known that one can obtain intensity versus time information of a light pulse using a streak camera.

Spectrographs are old in the art and have been in use for over 50 years. Streak cameras are about ten years old in the art and are used principally to directly measure the time dynamics of luminous events. A typical streak camera comprises an entrance slit which is usually rectangular, relay optics, a streak tube and appropriate sweep electronics. The streak tube contains a photocathode on the front, accelerating and sweeping electrodes and an output phosphor screen on the back. The relay optics serve to image the entrance slit onto the photocathode. The output streaked image is typically recorded using photographic film or video type readout systems. In an article entitled "An Ultrafast Streak Camera System" by N. H. Schiller, Y. Tsuchiya, E. Inuzuka, Y. Suzuki, K. Kinoshita, K. Kamiya, H. Iida and R. R. Alfano appearing in the June, 1980, Edition of *Optical Spectra*, various known streak camera systems are discussed. The article is incorporated herein by reference.

In the past, to spectrally resolve the kinetics of different emission components of a luminous event, a filter or spectrograph has been positioned in front of the entrance slit of the streak camera. This arrangement for obtaining spectral as well as temporal information simultaneously, has many limitations. Some of these limitations are as follows:
1. Limited spectral range covered;
2. Wide bandwidths about discrete wavelengths;
3. Non-continuous wavelength display;
4. Achromatic aberrations caused by the relay lens;
5. Limited spectral coverage requiring changing of relay optics;
6. Refocusing of input optics over well-defined spectral regions due to achromatic aberrations through relay lenses; and
7. Limited spectral transmission of relay optics.

In an article by G. W. Robinson, T. A. Caughey, R. A. Auerback and P. J. Harman entitled: "Coupling An Ultraviolet Spectrograph To A SC/OMA For Three Dimensional (n,I,t) Picosecond Fluorescence Measurements" appearing in *Multi-Channel Image Detectors* pp. 199–213, ACS Symposium Series 102, American Chemical Society, there is described an apparatus wherein a spectrograph is coupled to a streak camera in order to eliminate some of the above noted problems. The system employs an entrance slit 1000 microns high by 50 microns wide. Some of the shortcomings of the apparatus described in the article are:
1. It is not compact in size;
2. It involves rotating the grating by 90° from its normal orientation in a spectrograph relative to the streak camera;
3. It involves tilting the spectrograph body by 23° relative to the streak camera tube;
4. It is limited to spectral resolution of about 200Å,
5. It involves repositioning and alignment of the spectrograph portion of the apparatus and realignment of the collection optics each time the wavelength region to be examined is changed, and
6. It requires a flexible, non-rigid light tight shroud between the spectrograph and the streak camera.

In an article entitled "Picosecond Characteristics Of A Spectrograph Measured By A Streak Camera/Video Readout System" by N. H. Schiller and R. R. Alfano appearing in *Optical Communications*, Volume 35, number 3, pp. 451–454, 1980 which article is incorporate herein by reference, the problem of time broadening which may result from using spectroscopic instruments to measure picosecond luminous events is discussed.

In U.S. Pat. No. 4,162,851 there is disclosed a photometering method for multi-dimensional measurements wherein selected wavelengths of light are projected on a sample to permit three dimensional plots of a spectrum over a period of time to be obtained. In U.S. Pat. No. 3,765,769 there is described a device for producing a dynamic spectrogram and a technique for recording the component wavelengths and their relative intensity as a function of time. In U.S. Pat. No. 4,320,971 there is described a spectrophotometer operable to obtain a photoelectrical conversion signal corresponding to an arbitrarily selected wavelength from the signal time-sequentially produced from a one-dimensional image sensor. In U.S. Pat. No. 4,299,488 there is disclosed to a time-division multiplexed spectrometer operable to convert the output from a radiation source into a time-space and wavelength-division multiplexed pulse train. In U.S. Pat. No. 4,060,327 there is disclosed a spectrophotometer for receiving light from a test sample and measuring the radiant thereof as a function of wavelength, with the device providing outputs proportional to the intensity of the light rays at the different wavelengths received thereby. Other known patents relating to spectroscopy in general include U.S. Pat. Nos. 2,436,104, 2,823,577 and 3,385,160.

It is an object of this invention to provide a new and improved temporal spectral photometer.

It is another object of this invention to provide a temporal spectral photometer for use in obtaining spectral and temporal information simultaneously of an ultrafast pulse of luminescent light.

It is still another object of this invention to provide a temporal spectral photometer as described above which is compact and which provides spectral resolution of better than 10 Å and time resolution of better than about 10 ps.

It is a further object of this invention to provide a temporal spectral photometer as described above on which the spectrograph portion of the instrument is not tilted or rotated relative to the streak camera portion of the instrument and which does not require repositioning or realignment for different angular positions of the light dispersing element.

It is another object of this invention to provide a temporal spectral photometer or described above in which the spectrograph and streak camera portions may be enclosed in a non-flexible type housing.

It is a further object of this invention to provide an improved and novel arrangement for coupling a spectrograph to a streak camera.

It is still a further object of this invention to provide a temporal spectral photometer which includes an arrangement for aligning the entrance slit with the incoming light on a luminous sample.

It is another object of this invention to provide a temporal spectral photometer which includes an arrangement for aligning a streak camera with relay optics with incoming light on a luminous sample.

SUMMARY OF THE INVENTION

A compact high resolution temporal spectral photometer for use in obtaining spectral and temporal information simultaneiously of an ultrafast time scale pulse of light according to the teachings of the present invention comprises a housing having a pin hole entrance slit for admitting at least a portion of said light, a streak camera tube disposed inside said housing, said steak camera tube having a photocathode on the front and a phosphor screen on the rear, electronic circuit means for driving said streak camera tube, optical means disposed inside said housing for (1) imaging said pin hole slit onto the photocathode and (2) dispersing said light admitted through said pin hole slit into its component wavelength and, means for recording the output image formed on the phosphor screen of the streak camera tube.

The foregoing and other objects and advantages will appear from the description to follow. In the description reference is made to the accompanying drawings which form a part thereof, and in which is shown, by way of illustration, specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

In the drawings wherein like reference numerals represent like parts.

DETAILED DESCRIPTION OF PREFERRED EMBODIMENTS

The temporal spectral photometer of the present invention is an integral unit for displaying the intensity, as a function of wavelength and time from a luminous event, with a spectral resolution of better than 10Å and a time resolution of better than 10 ps. Because of its ability of continuously display wavelength, time and intensity it can easily resolve changes in these parameters. The grating portion of the instrument provides the spectral axis, the streak portion of the instrument provides the time axis while the analyzer portion of the instrument provides the photometric or intensity axis resulting in a single integrated and compact unit, displaying intensity vs. time vs. wavelength on a single sampling of the emission from an event. The light collection optics of the instrument comprises in an embodiment disclosed a 0.2 meter spectrograph with a 50 micron pin hole slit.

Figure 1:
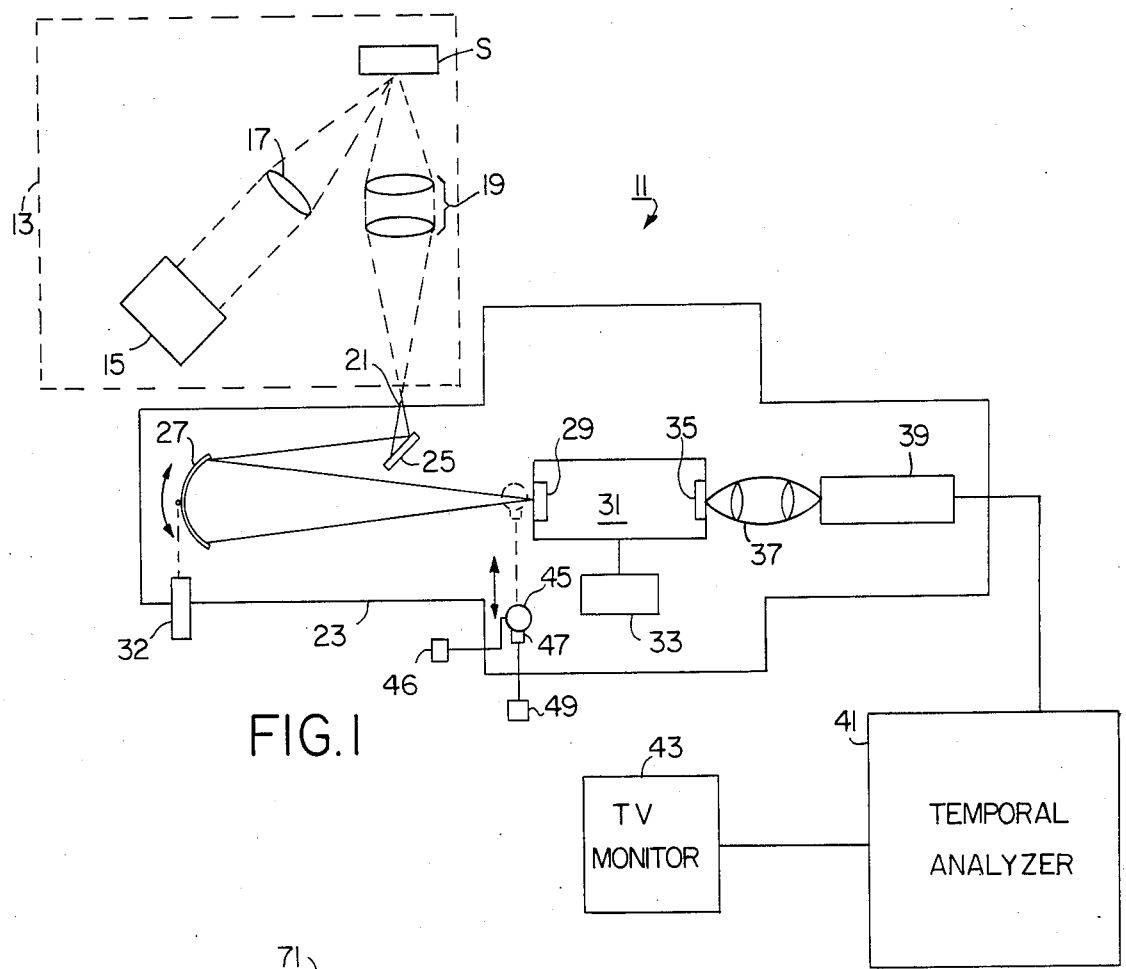
FIG. 1 is a schematic view of an embodiment of a temporal spectral photometer constructed according to the teachings of the present invention.

Referring now to the drawings, there is illustrated in FIG. 1 an embodiment of a temporal spectral photometer constructed according to the teachings of the present invention and identified generally by reference numeral 11.

Temporal spectral photometer 11 includes an associated illumination section 13 for exciting a sample S to emit luminescent radiation whose spectral and temporal characteristics are to be analyzed. Illumination section 13 includes a picosecond laser light source 15 for generating a collimated beam of light, the wavelength of the beam depending on the wavelength needed to excite the sample S to produce emission. Light source 15 may be for example a mode locked neodymium doped glass laser or a mode locked dye laser. The beam of light from source 15 is brought to focus as a small spot P on the samples S by a lens 17.

Luminescent radiation emitted from sample S is collected and brought to focus by a relay or collecting lens (or mirror) system 19 at a pin hole slit 21 formed on a rigid housing 23. Slit 21 is 50 microns in diameter but may be within the range of 10 to 100 microns.

Light admitted through pin hole slit 21 is deflected by a flat mirror 25 onto a 0.2 m curved holographic grating 27 which disperses the light impinging thereon into its component wavelengths. The dispersed light impinges on the surface of photocathode 29 of a streak camera tube 31. Grating 27 and streak camera tube 31 are positioned and spaced relative to each other and pin hole slit 21 so that pin hole slit is imaged onto photocathode 29. Since each wavelength present in the beam will be dispersed in a different direction, each wavelength will be brought to focus as a spot at a different location in photocathode 29. Grating 27 is mounted on a bracket (not shown) which may be rotated in the direction shown by the arrow through a micrometer 32 so that the spectral region impinging on the photocathode may be changed. Streak camera tube may be a model number N1357, N895, N1629 or similar such as used in the Hamamatsu System Inc. Streak Camera System Model Number C979, C1370 or C1587 or similar. Streak camera tube 31 is driven by an Avalanche circuit or sync sine type drive circuit 33. Since a pin hole type slit is employed and since the pin hole slit is along the optic axis of the instrument there is little or no smearing of the image of the slit on the photocathode caused by aberrations and astigmatism of the spectrograph section. The focal length of grating 27 is preferably in the range of 0.1 to 1.0 meters.

The resulting image formed on the phosphor screen 35 at the rear end of streak camera tube 31 is imaged by a lens system 37 onto the input surface of a silicon-intensified target (SIT) vidicon TV camera 39 which is coupled to a minicomputer temporal analyzer 41. Camera 39 may be a Hamamatsu model number C1000 and the temporal analyzer 41 may be a Hamamatsu System Inc. model number C1098, or C1440. The output data from temporal analyzer 41 is displayed as a profile of intensity versus time as a function of wavelength on a TV monitor 43.

Using a 0.2 m spectrograph with 200 lines/mm, 2 cm diameter grating, the calculated time spread for pulses centered at 180 nm and 850 nm are 2.6 ps and 10.5 ps, respectively. The spectral resolution is about 1 nm with a temporal resolution of approximately 10 ps. For the fastest sweep rate of the streak tube, the full time window is 500 ps and the full wavelength region displayed on the video monitor is 650 Å with the current configuration. The instrument enables the user to display luminous events on a picosecond time scale over a wide spectral range from 200 to 850 nm.

Temporal spectral photometer 11 further includes apparatus for aligning slit 21 with the spot O on sample S illuminated by the laser beam. The apparatus comprises a lamp 45, such as a small high intensity tungsten halogen lamp, coupled to a power supply (not shown) through a switch 46 and which is mounted on a bracket 47 which is movable from the position shown (in solid lines) in FIG. 1 to a position directly in front of the shutter (not shown) of the streak camera tube as shown by the dotted lines in FIG. 1 by any suitable electrical or mechanical drive system 49. To use the aligning apparatus, lamp 45 is moved to the position shown by the dotted lines and energized and the streak tube shutter is closed. Light from lamp 45 is imaged by grating 27 at the region of slit 21 and then in turn is imaged by lens system 19 as a small spot on sample. At the same time a small spot is formed on sample S by light from source 15. Alignment is then achieved by either adjusting the spot from slit 21 from lamp 45 on sample S to overlap the spot from laser 15 on sample S or by adjusting the spot from laser 15 on sample S to overlap the spot from slit 21 from lamp 45 through relay optics 19.

Figure 2:
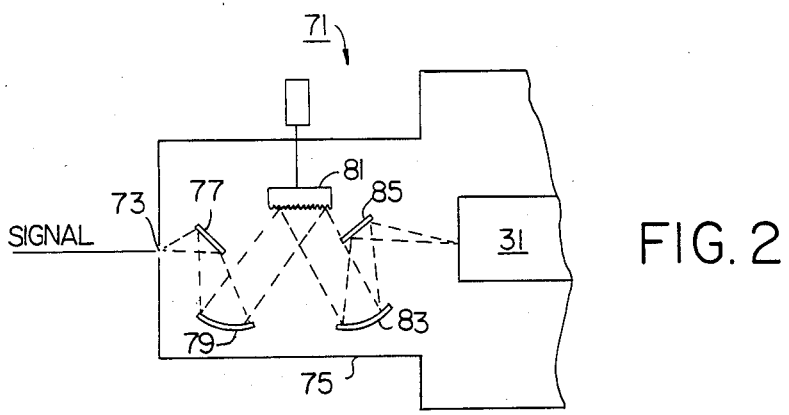
FIG. 2 is a schematic view of another version of the spectrograph portion of the temporal spectral photometer shown in FIG. 1.

Referring now to FIG. 2 there is illustrated another embodiment of the spectrograph portion of the instrument identified generally by reference numeral 71.

In this embodiment the pin hole entrance slit 73 is located at the front of housing 75 rather than at the side as in FIG. 1 and the optics portion which is in the form of a Czerny-Turner Spectograph includes a flat mirror 77, a collimating mirror 79 a flat grating 81 mounted for rotational movement in the direction shown by the arrow, a focussing mirror 83 and a flat mirror 85. Light admitted through pin hole slit 73 is deflected by flat mirror 77 onto collimated mirror 79 where it is collimated and impinges as a collimated beam on flat grating 81. The dispersed light from flat grating 81 is brought to focus by focusing mirror 83 as a small spot on the photocathode surface of the streak camera tube after it is deflected off of flat mirror 85.

As can be appreciated, since the admitted light through the pin hole slit is in the plane of incidence, the various mirrors need not be angularly readjusted for different angular settings of the grating. As can also be appreciated the time resolution is dependent on and limited by the focal length and grating size and the spectral and temporal resolution is dependent on the grating density. The grating density is preferably from 100 grooves/mm to 1200 grooves/mm. For example, for a 2 cm dia. apperture for a 200 groove/mm grating one has a 7 ps time resolution and a spectral span of 700° over 3 mm at the photocathode plane of the streak tube; and for a 1200 groove/mm grating has a time resolution of 42 ps with a wavelength span of 85° over 3 mm at the photocathode plane of the streak tube. It should further be noted that all mirrors are coated for the UV-visible region of the spectrum.

Figure 3:
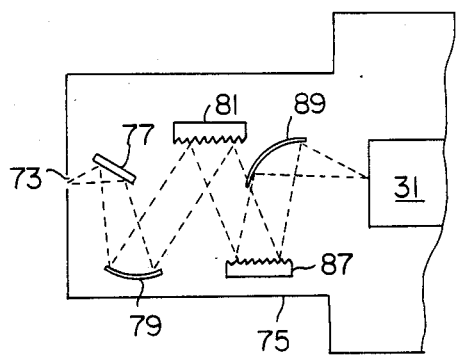
FIG. 3 is a schematic view of a modification of the apparatus illustrated in FIG. 2.

In FIG. 3 there is illustrated a modification of the apparatus shown in FIG. 2 wherein the mirror 83 is replaced with a flat grating 87 and mirror 85 is placed with a curved mirror 89. The two gratings (83 and 87) in series reduce (or compensate) for the temporal broadening caused by one grating by decreasing the path length of one ray relative to the other ray which is diffracted.

Although particular embodiments of the invention have been described and illustrated herein, it is recognized that modifications and variations may readily occur to those skilled in the art and consequently, it is intended that the claims be interpreted to cover such modifications and equivalents.

What is claimed is:

1. A temporal spectral photometer for use in obtaining spectral and temporal information simultaneously of an ultrafast pulse of light comprising:
   a. a housing having a pin hole type entrance slit for admitting at least a portion of said light,
   b. a streak camera tube disposed inside said housing, said streak camera tube having a photocathode on front thereof and a phosphor screen on the back thereof,
   c. electronic circuit means for driving said streak camera tube,
   d. optical means disposed inside said housing between said pin hole slit and said streak camera tube for forming an image of the pin hole slit onto the photocathode of the streak camera tube and at the same time dispersing the light admitted through said pin hole slit into its component wavelengths, and
   e. means for recording the resulting output image formed on the phosphor screen.

2. The temporal spectral photometer of claim 1 and wherein said pin hole slit is between around 10 microns and 100 microns in diameter.

3. The temporal spectral photometer of claim 2 and wherein said pin hole slit is around 50 microns in diameter.

4. The temporal spectral photometer of claim 2 and wherein said pin hole slit is disposed along the plane of incidence of the light.

5. The temporal spectral photometer of claim 2 and wherein the optical means and the streak camera tube are disposed along a common optical axis.

6. The temporal spectral photometer of claim 2 and wherein said optical means inside said housing comprise a curved holographic grating for dispersing light impinging thereon into its component wavelengths and imaging said entrance slit on said photocathode and a flat mirror for directing the light received through said pinhole slit onto said curved holographic grating.

7. The temporal spectral photometric system of claim 2 and wherein said optical means comprises a flat grating for dispersing light impinging thereon into its component wavelengths, a pair of flat mirrors for directing the light admitted through the pin hole slit onto the flat grating and from the flat grating onto the photocathode and a pair of curved mirrors for the collimating the light impinging on the grating from the pinhole slit and bringing the light dispersed from the grating into the photocathode.

8. The temporal spectral photometer of claim 2 and further including means for changing the wavelength region of the light impinging on the photocathode.

9. The temporal spectral photometer of claim 2 and wherein said means for recording the output image comprises a camera lens system and a video camera.

10. The temporal spectral photometer of claim 2 and further including aligning means for aligning the pin hole entrance slit relative to the incoming light.

11. The temporal spectral photometer of claim 2 and further including a picosecond light source comprising a mode locked laser for exciting a sample to produce emitted light in the picosecond time scale and collecting optics for collecting at least some of said emitted light and bringing said emitted light to focus at said pin hole slit.

12. A temporal spectral photometer for use in obtaining spectral and temporal information simultaneously of an ultrafast pulse of light emitted from a sample upon excitation thereof comprising:
   a. illumination means for exciting the sample over a defined area to emit said ultrafast pulse of light,
   b. an entrance slit for receiving at least a portion of said emitted pulse of light,
   c. optical relay means for imaging said sample over said area excited onto said entrance slit,
   d. a streak camera tube having a photocathode on the front thereof and an output screen on the back thereof,
   e. electronic circuit means for driving said streak camera tube,
   f. spectrograph means for dispersing the light admitted through said entrance slit into its component wavelengths and bringing a band of said wavelengths to focus on the photocathode of the streak camera tube, each wavelength in said band striking said photocathode at a different location,
   g. recording means for recording the resulting output image formed on the output screen of the streak camera tube, and
   h. housing means for housing said illumination means, said optical relay means, said streak camera tube, said spectrograph means and said recording means.

13. A temporal spectral photometer for use in obtaining spectral and temporal information simultanously of an ultrafast pulse of light emitted from a sample upon excitation thereof comprising:
   a. illumination means for exciting the sample over a defined area to emit said ultrafast pulse of light,
   b. an entrance slit for receiving at least a portion of said emitted pulse of light, said entrance slit being in the form of a pin hole,
   c. optical relay means for imaging said sample over said area excited onto said entrance slit,
   d. a streak camera tube having a photocathode on the front thereof and an output screen on the back thereof,
   e. electronic circuit means for driving said streak camera tube,
   f. optical imaging means for forming an image of the entrance slit onto the photocathode of the streak camera tube and at the same time dispersing the light admitted through said entrance slit into its component wavelengths,
   g. recording means for recording the resulting output image formed on the output screen of the streak camera tube, and
   h. housing means for housing said illumination means, said optical relay means, said streak camera tube, said optical imaging means and said recording means.

14. The temporal spectral photometer of claim 13 and wherein said pin hole is around 50 microns in diameter.

15. The temporal spectral photometer of claim 13 and wherein said illumination means comprises a laser light source for producing a collimated beam of light and a focusing lens for bringing said beam of light to focus as a spot on said sample.

16. The temporal spectral photometer of claim 15 and wherein said laser light source comprises an ultrafast laser.

17. The temporal spectral photometer of claim 13 and wherein the output screen of the streak camera tube is a phosphor screen.

18. The temporal spectral photometer of claim 13 and wherein the output screen of the streak camera tube is a solid state detector array.

19. The temporal spectral photometer of claim 13 and wherein said optical imaging means comprise a curved holographic grating for dispersing light impinging thereon into its component wavelengths and imaging said entrance slit on said photocathode and a flat mirror for directing the light received through said entrance slit onto said curved holographic grating.

20. The temporal spectral photometeric system of claim 13 and wherein said optical imaging means comprises a flat grating for dispersing light impinging thereon into its component wavelengths, a pair of flat mirrors for directing the light admitted through the entrance slit onto the flat grating and from the flat grating onto the photocathode and a pair of curved mirrors for collimating the light impinging on the grating from the entrance slit and bringing the light dispersed from the grating into the photocathode.

21. The temporal spectral photometer of claim 13 and further including fixed detent settings for changing the wavelength region of the light impinging on the photocathode.

22. The temporal spectral photometer of claim 13 and further including micrometer means for changing the wavelength region of the light impinging on the photocathode.

23. The temporal spectral photometer of claim 13 and wherein said means for recording the output image comprises a camera lens system and a video camera.

24. The temporal spectral photometer of claim 13 and further including aligning means for aligning the entrance slit relative to the emitted light from the sample.

25. The temporal spectral photometer of claim 23 and further including a temporal analyzer coupled to the output of the video camera and a TV monitor coupled to the output of the temporal analyzer.

* * * * *